United States Patent
May et al.

(10) Patent No.: US 6,730,923 B1
(45) Date of Patent: May 4, 2004

(54) TRANSMISSIVE CONVEYOR FOR USE IN PULSED LIGHT STERILIZATION

(75) Inventors: Richard May, San Diego, CA (US); Andrew H. Bushnell, San Diego, CA (US); William Fries, San Diego, CA (US)

(73) Assignee: PurePulse Technologies, Inc., San Diego, CA (US)

( * ) Notice: Subject to any disclaimer, the term of this patent is extended or adjusted under 35 U.S.C. 154(b) by 0 days.

(21) Appl. No.: 09/565,835

(22) Filed: May 5, 2000

(51) Int. Cl.[7] .................................................. A21D 6/00
(52) U.S. Cl. ............... 250/494.1; 250/435; 250/455.11; 250/492.1; 422/24; 426/120; 426/238; 426/248; 426/240; 435/173.3; 99/451
(58) Field of Search .................. 250/494.1, 455.11, 250/435, 492.1; 422/24; 435/173.3; 99/451

(56) References Cited

U.S. PATENT DOCUMENTS

| | | | |
|---|---|---|---|
| 4,424,188 A | 1/1984 | DiGeronimo | 422/20 |
| 4,800,090 A | 1/1989 | August | 426/243 |
| 4,842,880 A | 6/1989 | Creason et al. | 426/303 |
| 4,871,559 A | 10/1989 | Dunn et al. | 426/248 |
| 4,910,942 A | 3/1990 | Dunn et al. | |
| 4,983,411 A | 1/1991 | Tanaka et al. | 426/234 |
| 5,034,235 A | 7/1991 | Dunn et al. | 426/238 |
| 5,489,442 A | 2/1996 | Dunn et al. | 426/248 |
| 5,658,530 A | 8/1997 | Dunn | 422/24 |
| 5,786,598 A | 7/1998 | Clark et al. | 250/455.11 |
| 5,900,211 A * | 5/1999 | Dunn et al. | 422/24 |
| 5,925,885 A * | 7/1999 | Clark et al. | 250/492.1 |
| 5,958,336 A | 9/1999 | Duarte | |
| 6,150,663 A * | 11/2000 | Rosenthal | 250/435 |
| 6,433,344 B1 * | 8/2002 | Salisbury et al. | 250/455.11 |

FOREIGN PATENT DOCUMENTS

| | | |
|---|---|---|
| WO | WO 88 03369 A | 5/1988 |
| WO | WO 94 24875 A | 11/1994 |
| WO | WO 97 43915 A | 11/1997 |

\* cited by examiner

*Primary Examiner*—John R. Lee
*Assistant Examiner*—Zia R. Hashmi
(74) *Attorney, Agent, or Firm*—Thomas F. Lebens; Fitch, Even, Tabin & Flannery

(57) ABSTRACT

An apparatus for carrying a target object having a plurality of surfaces, within a pulsed light sterilization chamber including a treatment zone within which pulsed sterilizing light is emitted, comprises: a transmissive carrier within the treatment zone detachably coupled to the target object, the transmissive carrier having a transmissivity of at least about 10% to light within the 250 to 350 nm wavelength range; and moving means coupled to the transmissive carrier for moving the target object on the transmissive carrier through the treatment zone, the plurality of surfaces of the target object being sterilized by the pulsed sterilizing light in the treatment zone. A system for sterilizing a target object having a plurality of sides, comprises: a pulsed light sterilization chamber comprising a treatment zone and means for emitting pulsed sterilizing light within the treatment zone; a moving means; and a transmissive carrier within the treatment zone detachably coupled to the target object, and coupled to the moving means which moves the target object on the transmissive carrier through the treatment zone, the plurality of sides of the target object being sterilized by the pulsed sterilizing light through the treatment zone.

25 Claims, 5 Drawing Sheets

TRANSMISSIVE CONVEYOR FOR USE IN PULSED LIGHT STERILIZATION

BACKGROUND OF THE INVENTION

The present invention relates to sterilization of products, and more particularly to sterilization of products using pulsed, short duration, polychromatic, incoherent light. Even more particularly, the present invention relates to sterilization of products wherein a transmissive carrier is employed to transport the product through a treatment zone thereby permitting complete sterilization of the product by avoiding shadowing of the pulsed polychromatic incoherent light.

The present invention addresses the particular need which exists for improved methods and apparatus for efficiently sterilizing or reducing the microbiological burden on the surfaces of or throughout the volume of anything requiring sterilization. Examples of surfaces and volumes of products needing sterilization include surfaces of solids and/or solids within liquid products, surfaces or volumes of food stuffs, surfaces or volumes of containers for food stuffs, surfaces of medical devices, surfaces of packages, and volumes of liquids.

By way of example, any varieties of foods (such as fresh fish) and medical products, have a relatively limited storage time before being subject to microbial and/or enzymatic spoilage, which limits the distribution and marketing. Further in the case of medical products, in particular, microbial deactivation must be achieved to medically acceptable sterility levels. Improved methods and apparatus suitable for extending the shelf life of perishable foods, medical devices and any other products requiring sterilization are therefore desirable.

Improved methods and apparatus for reducing or eliminating biological activity without degradation or other undesirable secondary effects on the product is also desirable.

An improved apparatus and method for sterilization of non-food products such as medical devices, is particularly desirable for research apparatus such as chemical reagents, plates, and test tubes which must be sterile to be used in unlimited medical or research procedures.

The-photo biological effects of light, including visible light (380–780 nm), near ultraviolet light (300–380 nm) and far ultraviolet light (190–300 nm), have been studied for many years, for example, as reported in Jagger, J., "Introduction to Research in Ultraviolet Photo Biology", Prentice Hall, Inc., 1967, and efforts have been made to employ light for sterilization.

U.S. Pat. No. 5,034,235 (hereinafter the '235 patent, issued Jul. 23, 1991 to Dunn, et al.) incorporated herein by reference, teaches utilizing intense, short duration pulses of UV-rich polychromatic, incoherent light in order to sterilize a surface of a food product.

Problematically, the use of pulsed light for sterilization of a product surface (typically meaning an exterior solid surface thickness to about 0.1 mm) is only as effective as the ability of the pulsed light to penetrate through any obstructions to the surfaces or volumes to be sterilized, that is, all areas to be treated must be fully contacted by the sterilizing levels of light.

This means, for example, that if the target object is a fluid, a fluid having a higher degree of transparency to a broad range of wavelengths, such as water and air, the target object will be more effectively treated by a given level of light than a more opaque fluid such as wine or sugar solution. A more opaque fluid solution would require either a smaller treating volume or a higher level of light, both of which reduce efficiency and in the later case, risk damage to the target object by the sterilizing level of light. Similarly, if the target object is a solid object or material, such as a food product or medical device, the solid object must be contacted by the pulsed light sufficiently, on all surfaces, to be sterilized, without shadowing of any such surfaces.

U.S. Pat. No. 4,871,559 (hereinafter the '559 patent, issued Oct. 3, 1989 to Dunn et al.), incorporated herein by reference, teaches that certain solid materials such as cut, sliced or particulate foods (e.g., dried vegetables) may be treated in a fluid suspension medium in order to avoid shadowing effects. However, this method obviously is limited, in its usefulness, to those products that may be processed and suspended in fluid.

With respect to solid objects such as a container being treated by pulsed light, the '559 patent teaches that such an object may be treated by rotating or turning the object during a multiple exposure treatment involving a series of light pulses; or by letting the object freely fall through a treatment zone surrounded by flashlamps so that substantially the entire surface of the product is subjected to simultaneous treatment.

The '559 patent also teaches that the solid object or material may be packaged in a transparent wrapping material prior to the pulsed light treatment to reduce the shadowing effect as compared to a more opaque wrapping material used around the solid object.

U.S. Pat. No. 5,489,442 (hereinafter the '442 patent, issued Feb. 6, 1996 to Dunn, et. al.), incorporated herein by reference, similarly teaches methods for treatment of solid objects. In particular, the '442 patent describes the use of rollers or shakers to rotate the product between two or more flashes, or that the product may be rotated manually.

Unfortunately, these prior art methods of rotating the solid product or material, (such as a container or wrapped package), while sterilizing, can be ineffective unless a large number of pulses are used while the solid product is moving within the treatment area (or treatment zone) to allow all of its surfaces to be exposed to the sterilizing light. Meanwhile, some of the sterilizing light will be wasted on opaque surfaces shadowing the product to be sterilized. Consequently, a lesser throughput capacity results and cost, energy and time parameters are increased.

Thus, it is desirable to have a method and apparatus for transporting a solid product through a treatment zone of a sterilization chamber without the need for product manipulation within the zone or for multiple treatment exposures, such that a higher throughput capacity is thereby achieved, while decreasing the cost, time and energy required for the sterilization.

The present invention advantageously addresses the above and other needs by providing a method and apparatus for sterilizing a product with pulsed light while avoiding shadowing of the pulsed light upon the product being sterilized.

U.S. application Ser. No. 09/326,168, filed Jun. 4, 1999 of Clark, et al., for PARAMETRIC CONTROL IN PULSED LIGHT STERILIZATION, U.S. application Ser. No. 08/846,102 of Clark, et al., for PARAMETRIC CONTROL IN PULSED LIGHT STERILIZATION, now U.S. Pat. No. 5,925,885, and U.S. application Ser. No. 08/651,275, of Clark, et al., for STERILIZATION OF PACKAGES AND THEIR CONTENTS USING HIGH-INTENSITY, SHORT- DURATION PULSES OF INCOHERENT, POLYCHROMATIC LIGHT IN A BROAD SPECTRUM, now U.S. Pat. No. 5,786,598, are all incorporated herein by reference.

SUMMARY OF THE INVENTION

The present invention advantageously addresses the needs above as well as other needs by providing an apparatus for transporting a target object within a pulsed light sterilization chamber via a transmissive carrier which allows for sterilization of the target object without obstruction or shadowing by the transmissive carrier. The present invention also provides for a system for sterilizing the target object using such transmissive carrier to transport the target object through the system.

One embodiment of the invention is characterized as an apparatus for carrying a target object having a surface, within a pulsed light sterilization chamber within which pulsed sterilizing light is emitted. The apparatus comprises: a transmissive carrier within the treatment zone, the transmissive carrier engaging the target object, the transmissive carrier having a transmissivity of at least about 10% between 250 and 350 nm wavelength; and moving means coupled to the transmissive carrier for moving the target object by moving the transmissive carrier through the treatment zone, the surface being sterilized by the pulsed sterilizing light, at least a portion of the pulsed sterilizing light passing through the transmissive carrier before reaching the target object.

In another embodiment, the invention may be characterized as a system for sterilizing a target object having a surface. The system comprises: a pulsed light sterilization chamber comprising a treatment zone and means for emitting pulsed sterilizing light within the treatment zone; a moving means; and a transmissive carrier within the treatment zone, the transmissive carrier engaging the target object, and being coupled to the moving means, the moving means moving the target object by moving the transmissive carrier through the treatment zone such that the surface of the target object is sterilized by the pulsed light in the treatment zone, at least a portion of the pulsed light passing through the transmissive carrier before reaching the target object.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE PREFERRED EMBODIMENTS

The following description is of the presently contemplated best mode of practicing the invention and is not to be taken in a limiting sense, but is made merely for the purpose of describing the general principles of the invention. The scope of the invention should be determined with reference to the claims.

Figure 1:
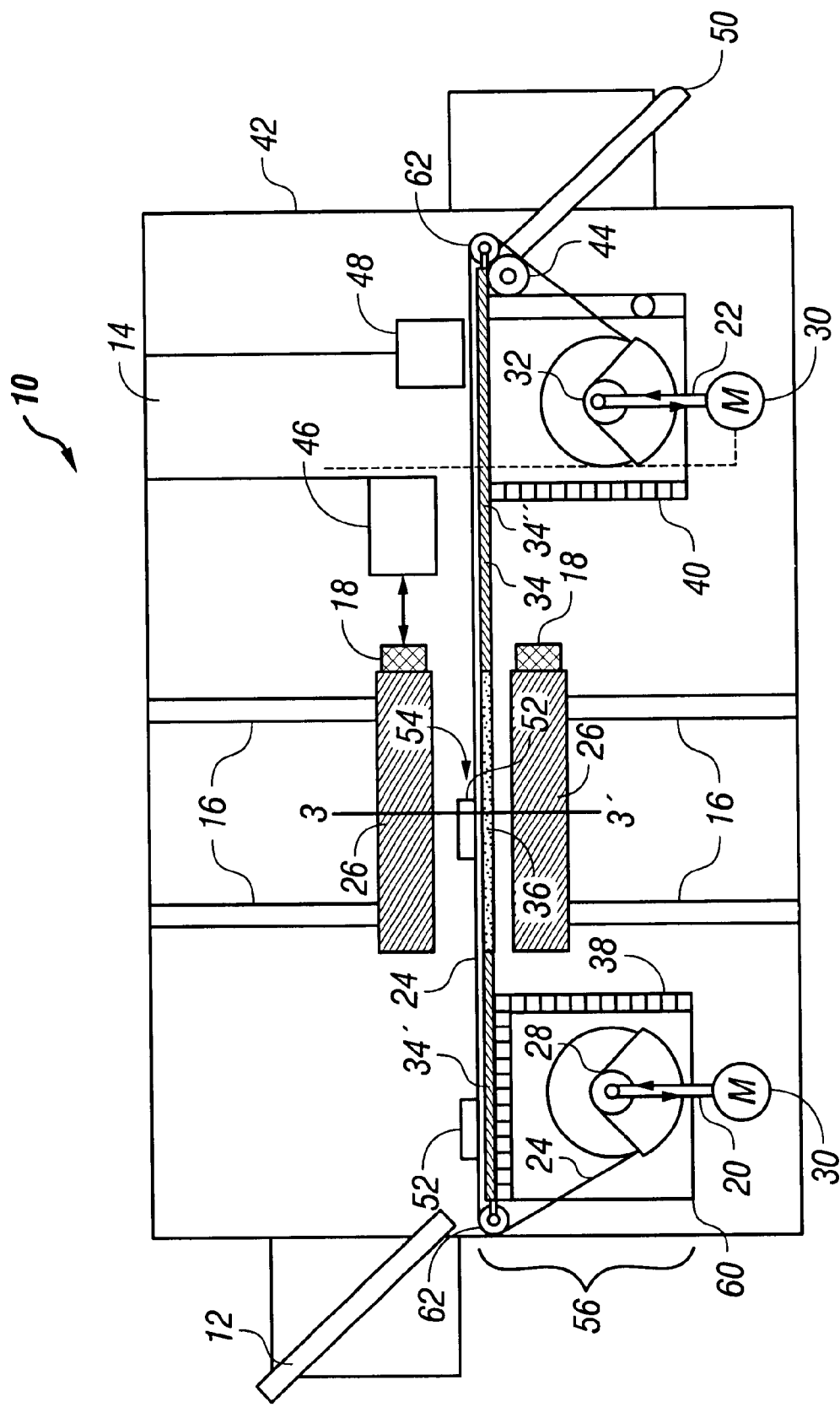
FIG. 1 is side cross-sectional view of one embodiment of a pulsed light sterilization chamber and system, in accordance with the present invention, in which a thin film rolled onto two opposing wheels and passing through a treatment zone is used as a transmissive carrier for pulsed light sterilization of a product.

Referring first to FIG. 1, a pulsed light sterilization system 10 is shown, in accordance herewith, that employs one embodiment of a transmissive carrier for carrying a target object 52 through a pulsed light treatment chamber 14.

The pulsed light sterilization system 10 comprises: an entrance drop 12 with a flap (not shown); the pulsed light sterilization chamber 14; a flashlamp unit 26 comprising a plurality of flashlamps (and reflectors as shown later in FIG. 3); a plurality of flashlamp supports 16; an electronic interface 18 for each flashlamp unit 26; an initial wheel 20; a take-up wheel 22; a thin film 24; a first rolled portion 28 of the thin film 24; a moving mechanism (or moving means) 30; a second rolled portion 32 of the thin film 24; a slide deck 34; a transmissive support 36; an initial wheel shielding 38; a take-up wheel shielding 40; reflective walls 42; a shaft encoder 44, a pulser 46 (with a programmable logic controller, PLC), a packager 48; and an exit drop 50.

Structurally, the entrance drop 12 comprises an entrance drop, including an entrance slide, connecting an outside environment to an interior of the pulsed light sterilization chamber 14. Preferably, the entrance drop 12 further comprises a door or flap to the pulsed light sterilization chamber 14, through which the target object 52 must pass. The door or flap rests horizontally when closed and covers an upper side of the entrance drop 12, above the entrance slide. The entrance drop 12, together with the door or flap, encases the entrance slide and forms a light-tight entry into the pulsed light sterilization chamber 14.

The pulsed light sterilization chamber 14 may preferably be enclosed by reflective walls 42, also contributing to the light-tight structure of the pulsed light treatment chamber. The pulsed light sterilization chamber 14 includes a treatment zone 54 for pulsed light sterilization of the target object 52 and a transport system 56 (comprising the thin film 24, the initial wheel 20, the take-up wheel 22, and the moving means 30) for transporting the target object 52 through the pulsed light sterilization chamber 14, into and out of the treatment zone 54.

The treatment zone 54 preferably lies in a region surrounded by a plurality of sterilizing light sources, such as the plurality of flashlamps within the flashlamp units 26.

In one embodiment, the flashlamp unit 26 includes a plurality concave reflectors (shown later in FIG. 3) each comprising an elongated trough having a curved cross-section, such as in the shape of a half ellipse, a parabola, a hyperbola or a similar curved shape. Each concave reflector contains at least one flashlamp (shown later in FIG. 3) positioned parallel to the concave reflectors's major axis (horizontal and parallel to the paper in FIG. 1). Each flashlamp radiates pulsed light from a position roughly equidistant from the target object 52, so that an approximately homogeneous light intensity can be maintained over a plurality of surfaces of the target object 52. Shaping the reflectors can also be customized to help accomplish homogeneous intensity. The flashlamps themselves can also take any of a variety of geometries or configurations, such as "U" shaped flashlamps, tubular (or linear) flashlamps or any combination of the above geometries or other geometries also known in the flashlamp art. An assortment of styles of such flashlamps may be obtained from PurePulse Technologies, Inc., located in San Diego, Calif.

Figure 2:
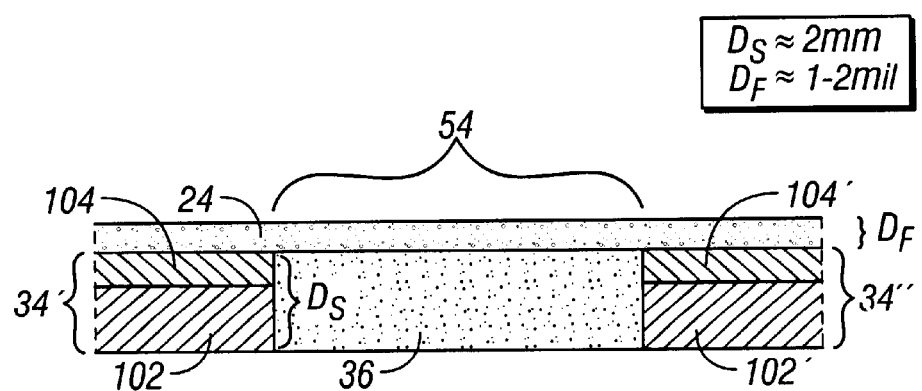
FIG. 2 is a detailed (blow-up) side view of a section of a portion of the pulsed light sterilization chamber of FIG. 1, illustrating one embodiment of the treatment area (or treatment zone)
Figure 3:
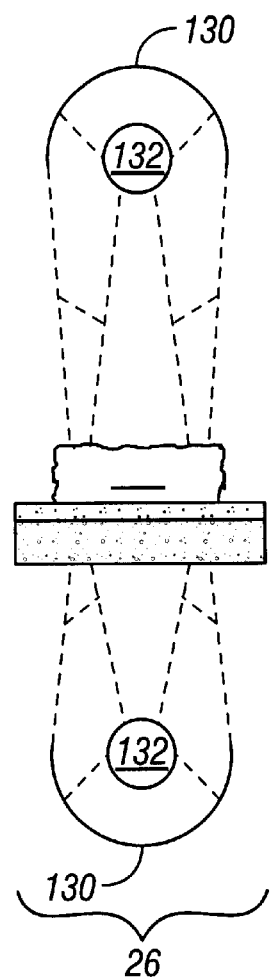
FIG. 3 is a cross sectional view, taken along line 3–3' of FIG. 1 (perpendicular to direction of viewing of both FIG. 1 and FIG. 1B) illustrating a system of flashlamps and reflectors that may be employed in the sterilization chamber of FIG. 1.

In practice, a pulsed light unit such as PUREBRIGHT PBS-1, available from PurePulse Technologies, Inc. of San Diego, Calif. may be used to generate intense, short duration pulses of broad spectrum polychromatic incoherent light such as may be used by the sterilization chamber of FIGS. 1, 2 or 3.

The pulsed light unit, such as the PUREBRIGHT system cited above, includes a pulsing device 46, with a DC power supply that charges energy storage capacitors; a switch used to discharge the capacitors; a trigger circuit used to fire the switch at pre-programmed time intervals, in response to sensors that detect the position of the target object 52 to be treated, or in response to a button being depressed; and a set of high voltage coaxial cables carrying the discharged pulses from a capacitor-switch assembly to the flashlamps. The flashlamp units 26 optionally include from one to eight flashlamps mounted in metal reflectors so as to direct the polychromatic light emitted from the flashlamps toward the target object 52.

Other embodiments of the pulsed light unit and flashlamp unit 26 are also conceivable within the scope and principles of the present embodiment wherein a variety of light intensities or amount of total sterilizing pulses may be required. For example, one other preferred embodiment employs swivelable flashlamp units.

Figure 1B:
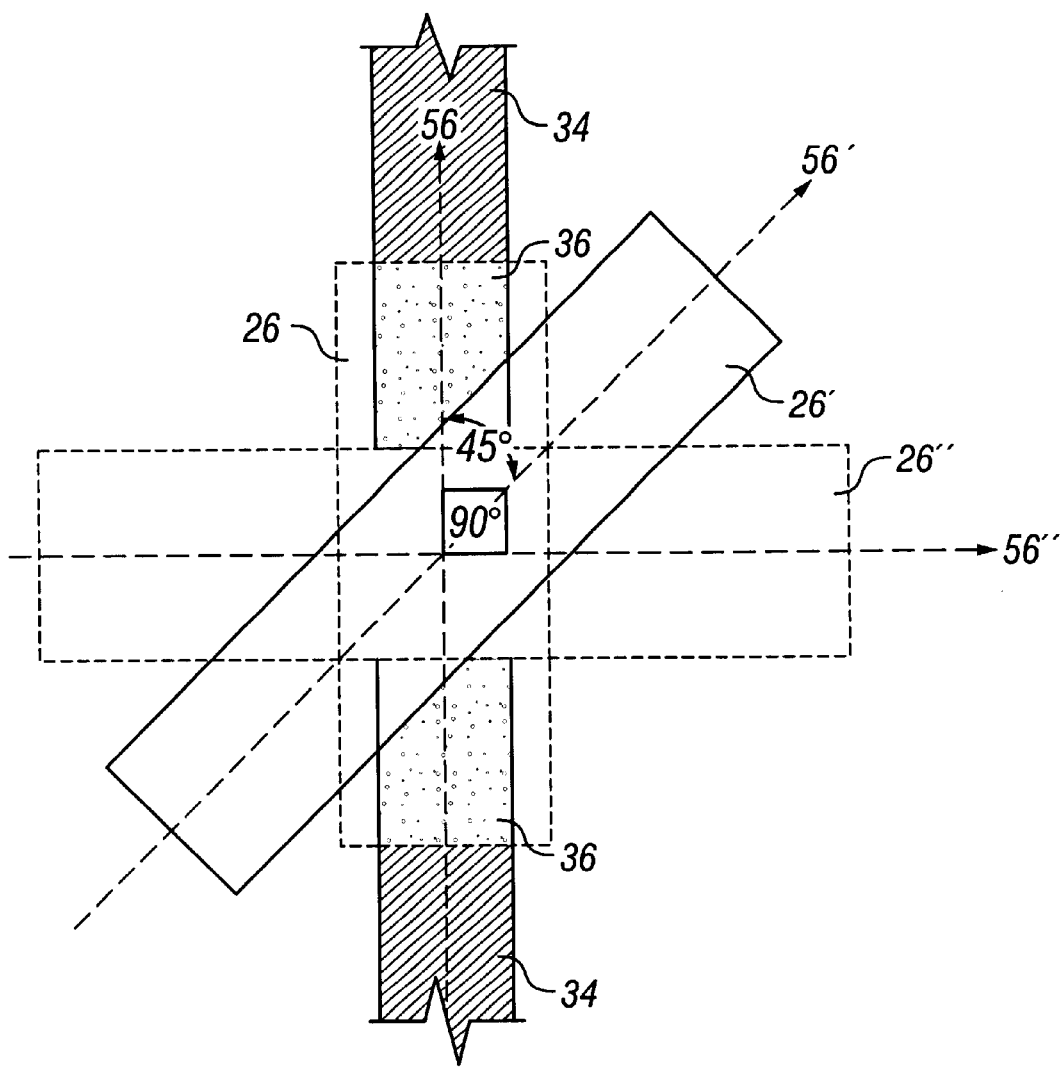
FIG. 1B is a top planar view of a swivelable flashlamp unit, which may be employed in the system of FIG. 1.

Referring next to FIG. 1B, a top planar view is illustrated of one preferred embodiment of the flashlamp units 26, wherein the flashlamp units 26 may be swivelled within a plane parallel to the direction of travel of the target object as it traverses the treatment zone and thereby can be adjusted to a particular angle with respect to a major axis of the flashlamp units 26 as shown in FIG. 1.

The ability to swivel the flashlamp units 26 allows the user to adjust an amount of pulsed light which is incident upon the target object 52 throughout its passage within the treatment zone 54, as well as an energy density ($J/cm^2$) deposited on the plurality of surfaces of the target object 52 by the pulsed light. In this manner, a total amount of sterilization through the treatment zone 54 may be adjusted without having to modify speed of the conveyor (e.g., the thin film 24) or parameters of the pulser 46 (such as pulse duration, intensity of each pulse, or number of pulses, etc . . . ).

As an example of its operation, the flashlamp unit 26 is moved from its original position for maximum light incidence (as in FIG. 1), wherein the flashlamp unit 26 has a major axis 56 lying coincidentally in a direction of a first major axis 56 of the transmissive support 36 and of the slide deck 34, to an intermediary position for moderate light incidence, shown by a flashlamp unit 26', wherein the flashlamp unit 26' has a second major axis 56' lying 45° from the first major axis 56'.

For minimal light incidence, the flashlamp unit 26' may be moved into position shown by a flashlamp unit 26" such that it has a third major axis 56" lying 90° from the first major axis 56 and 45° from the second major axis 56'.

Referring back to FIG. 1, irrespective of the particular arrangement or shapes of the flashlamps or the concave reflectors, the flashlamp units 26 are each coupled to the pulser 46 and the electronic interface 18 is coupled to each of the flashlamp units 26 for sending control signals (for controlling the pulsed sterilized light and position of the flashlamp units 26) to the flashlamp units 26 from the pulser 46.

A shaft encoder 44 may optionally be coupled to one of the rollers 62 to measure a rotational speed of the rollers 62. The shaft encoder 44 sends out a pulse train to the pulser 46, whose frequency is an indication of the rotational speed of the roller 62 to which it is coupled. When a predetermined number of pulses is counted by the pulser 46, the pulser 46 flashes the lamps and starts counting again until a next flash is generated after another predetermined number of pulses, and so forth.

The rollers 62 rotate as the thin film 24 is pulled by the take-up wheel 22, which rotates in response to the moving mechanism 30. The moving mechanism 30 may be a rotation device, such as a spinning shaft, belt gear, chain or other linkage coupled to a motor, that is rotatably coupleable with the initial and take-up wheels 20, 22. The moving mechanism 30 may be rotatably coupled to the take-up wheel 22, so as to allow forward rotation of the initial wheel 20 and the take-up wheel 22. Alternatively, the moving mechanism 30 is rotatably coupled to both the initial wheel 20 and the take-up wheel 22 so as to enable controlled rotation of the thin film 24 in either direction and from either of the initial wheel 20 and the take-up wheel 22 to the other.

In practice, before starting the system of FIG. 1, the moving mechanism 30 rotates the take-up wheel 22 clockwise to spool the thin film 24 from the initial wheel 20, causing the initial wheel 20 to rotate clockwise as well, thereby causing the thin film 24 to move from a left side to a right side of the system as shown in FIG. 1. When the initial wheel 20 has used up its first rolled portion 28, and an operator wishes to reuse the thin film 24, the moving mechanism 30 rotates the initial wheel 20 counter-clockwise to respool the initial wheel 20 for reuse.

The thin film 24 is used as a transmissive carrier for carrying the target object 52 through the treatment zone 54 while simultaneously avoiding shadowing on the target object 52 from the pulsed light emitted by the flashlamp units 26.

In one embodiment, the thin film 24 is a transmissive film which preferably has a transmissivity (defined as total throughput of light within a prescribed bandwidth of light) of at least over 10% in a 250 nm to 350 nm wavelength range and more preferably maintains at least this level of transmissivity through at least one or more, e.g., more than five or ten, e.g., more than twenty sterilization treatments comprising, e.g., at least 1 flash at 300 $\mu$s/flash of broad-spectrum polychromatic light having at least a 0.25 $J/cm^2$ corresponding energy density at a 170–2600 nm broadband bandwidth within the treatment zone.

In particular, the thin film 24 is sufficiently heat tolerant and ultraviolet tolerant to maintain its level of transmissivity through at least one sterilization treatment, and preferably through several sterilization treatments. This is an important feature of the thin film 24 as it is susceptible to degradation with prolonged exposure to the pulsed light. In general the thin film 24, made from any polyethylene, polypropylene, nylon, or aclar, and that is less than about 5 mils thick, will degrade by about 5% after being exposed to about 20 flashes of the 300 µs/flash broadband polychromatic light of the corresponding energy density equal to at least 2 J/cm² at its plurality of surfaces at 170–2600 nm broadband bandwidth.

In certain instances, depending upon the application, the thin film 24, may be re-used, if not too degraded for the particular application. In such case, the initial wheel 20 can be respooled as described above, by pulling the thin film 24 from the second rolled portion 32 to the first rolled portion 28.

Optionally, if the user does not wish to re-use the thin film 24 after it has been exposed to one full treatment (as defined above), the user may replace the thin film 24 by placing a new first rolled portion 28 upon the initial wheel 20 and threading it attachably to the take-up wheel 22. Also, optionally, an entire new tape cassette 60 comprising both the initial wheel 20 and the take-up wheel 22 may be employed by threading the thin film 24 around rollers 62 and the slide deck 34 and transmissive support 36 in a manner somewhat (but not exactly) akin to a music tape cassette threaded through a tape player. This allows for increased versatility in how the thin film 24 can be employed.

Many other embodiments of the invention are conceivable in which various different levels of transmissivity in a wavelength range of between about 250 and 350 nm are used by the sterilization chamber 14.

The thin film 24 may be made of various materials, well known to those of skill in the art, tending to be transmissive in the UV and visible part of the spectrum. As described earlier, some materials having this property which can be used in the thin film 24 include, but are not limited to: polyethylene, polypropylene, nylon and aclar.

Preferably, the thin film 24 material and thickness selected is durable enough to withstand a weight of the target object 52 and frictional forces experienced in transporting the target object 52 through the sterilization chamber 14, yet is flexible enough to easily wind around the initial wheel 20 and the take-up wheel 22 and is thin enough to minimize interference with the sterilizing light.

For example, as described earlier, the thin film 24 preferably has a thickness of less than about 5 mils and most preferably is about 1 to 2 mils in thickness and may be made of any of the above listed materials.

In the preferred embodiment illustrated in FIG. 1, the thin film 24 is placed in a configuration such that it is used as a conveyor belt, transporting the target object 52 through the treatment zone 54, wherein the thin film 24 includes the first rolled portion 28 rolled upon the initial wheel 20, and the second rolled portion 32 rolled upon the take-up wheel 22. In this way the thin film 24 is spooled from the first rolled portion 28 to the second rolled portion 32.

Optionally, the initial wheel 20 and the take-up wheel 22 are shielded by reflective shielding 38, 40 so as to avoid reduction in strength and/or transmissivity from stray ultraviolet radiation escaping from the treatment zone 54.

Alternatively, only one of the initial or take-up wheels 20, 22 is shielded, such as the initial wheel 20, such as where the thin film 24 is a single use carrier, thus obviating the need to preserve the used thin film 24 on the take-up wheel 22. Shielding can substantially enclose one or both of the initial or take-up wheels 20, 22, or just intercept radiation from a portion of a surrounding volume around one or both of the initial or take-up wheels 20, 22.

When positioned within the sterilization chamber 14 as shown in FIG. 1, the thin film 24 of the present embodiment preferably extends from between the first rolled portion 28 and the second rolled portion 32 spanning from underneath the entrance drop 12, across the treatment zone 54, and to the exit drop 50.

The slide deck 34 is positioned below the thin film 24 thereby giving support to the thin film 24. The slide deck 34 comprises two deck portions for supporting and conveying the thin film 24 to and from the treatment zone 54, so that the thin film 24 maintains its strength and ability to transport the target object 52 to the treatment zone 54. An entrance deck portion 34' of the slide deck 34 extends from below the entrance drop 12 and abuts the transmissive support 36. An exit deck portion 34" of the slide deck 34 extends from the transmissive support 36 to above an exit drop 50.

The transmissive support 36 is coupled on one side to the entrance deck portion 34' and on an opposing side to the exit deck portion 34". The transmissive support 36 spans a length of the treatment zone 54 and is positioned between the two flashlamp units 26 such that the pulsed sterilizing light from the flashlamp units is not shadowed in the treatment zone 54. The transmissive support 36 may be positioned any distance from each of the two flashlamp units 26, depending upon the required application for sterilization and the target object 52 being sterilized. Preferably, the transmissive support 36 is positioned such that the intensity of light at upper and lower surfaces of the target object 52 is approximately equal, e.g., the transmissive support 36 may be positioned such that the target object 52 is approximately equidistant from each of the two flashlamp units 26.

During operations to sterilize the target object 52 in the sterilization chamber 14, the transport system 56 moves the thin film 24 through the pulsed light sterilization system 10 by the moving mechanism 30. The moving mechanism 30, which may be a rotating pin belt, or shaft with motor, is coupled to the take-up wheel 22 or to both the initial wheel 20 and take-up wheel 22, depending upon the type of application and the requirement for reusing the thin film 24, and imparts a rotational force to the initial wheel 20 or the take-up wheel 22, thereby winding the thin film 24 onto the initial wheel 20 or the take-up wheel 22 (and thus off of the other of the initial wheel 20 and the take-up wheel 22) so as to move the thin film 24 through the treatment zone 54, across the slide deck 34 and the transmissive support 36.

During operations in a forward direction, the first rolled portion 28 on the initial wheel 20 is moved from the first rolled portion 28 to the underneath of the entrance drop 12, then moved across the entrance deck portion 34', across the transmissive support 36, across the exit deck portion 34" to over the exit drop 50, and to the second rolled portion 32 on the take-up wheel 22. During operations in a reverse direction, thin film 24 from the second rolled portion 32 is moved to underneath the exit drop 50, then across the exit deck portion 34", across the transmissive support 36, across the entrance deck portion 34' to under the entrance drop 12 to the first rolled portion 28.

Also during operations (in a forward direction), and while the thin film 24 is moving, the target object 52 is dropped through the entrance drop 12 and falls onto the thin film 24 passing over the entrance deck portion 34' underneath the entrance drop 12. The target object 52 is conveyed or moved by the thin film 24 as the thin film 24 is moved into the treatment zone 54.

Once inside the treatment zone 54, the target object 52 is exposed to one or more pulses of high intensity, short-duration polychromatic light from the flashlamp units 26 and then continues moving on the thin film 24. The transmissive support 36 supports a weight of the target object 52 on the thin film 24 and allows the thin film 24 to slide thereon.

During operations, the flashlamp units 26 operate according to a programmable logic controller (PLC) (not shown), inside the pulser 46 and electronic interfaces 18. The PLC stores user-defined parameters that define the operation of the flashlamps. The user-defined parameters pertain to several parametric conditions for operating the flashlamp units 26 which control how much pulsed light sterilization to apply and how, and, optionally, whether to rotate the flashlamp units 26 and by what angle of rotation.

Examples of some of the user-defined parameters include: 1) charge voltage; 2) a number of pulses; 3) an energy density (e.g., in Joules/cm$^2$) deposited by the pulsed light; and 3) a set speed of the target object 52 through the treatment zone 54.

For example, in one embodiment, the flashlamp units 26 operate to emit pulsed polychromatic, incoherent light with the following parameters or characteristics known to have good sterilizing effects. From 1 to 20 pulses of polychromatic incoherent light are emitted by the flashlamp units 26 during a transit of the target object 52 across the transmissive carrier. Generally, the pulses of polychromatic incoherent light are in a broad spectrum from 170 nm to 2600 nm using short pulses of durations from 0.001 to 100 milliseconds, at a high intensity, e.g., corresponding to an energy density of from 0.01 to 5 Joules/cm$^2$ at a surface of the target object 52.

In another alternative embodiment, a monochromatic (e.g., laser) light source that is either pulsed or continuous, may be used.

Depending upon the application, a polychromatic or monochromatic (e.g., laser) source that is either pulsed or continuous, may be used.

Depending upon the application, a polychromatic or monochromatic (e.g. laser) source may be used for an extended period of time if more sterilization is needed, and depending upon the intensity of the pulsed light.

Examples of extended durations of time which may be used in conjunction with the above parameters known for good sterilizing effects (170–2600 nm with pulses from 0.001 to 100 milliseconds with corresponding energy density of about 0.01 to 5 J/cm$^2$) for certain applications include periods of time lasting more than one (1) second, ten (10) seconds or several minutes even. A narrower spectrum may also be used, alternatively. For example, a pulse duration of 1/10 seconds for one second long would allow ten continuous total pules, if pulsed without time lapses between pulses, to be administered to the target object 52.

Alternatively, while the target object 52 is still within the pulsed light sterilization chamber 54, it may be wrapped in sterile wrap or packaged before it exits through the exit drop via the packager 48.

Referring next to FIG. 2, a partial crosssectional side view is shown of different sections of the pulsed light sterilization chamber 14 of the pulsed light sterilization system of FIG. 1 near the treatment zone 54. A portion of the entrance deck portion 34' of the slide deck 34 comprises two layers, a substrate 102, and a Teflon coating 104. The thin film 24 is also shown as it slides on top of the entrance deck portion 34' as it approaches the treatment zone 54 above the transmissive support 36 of the pulsed light sterilization chamber 14. The entrance deck portion 34' and the transmissive support 36 are coupled to an interface between a "downstream" edge of the entrance deck portion 34' and an "upstream" edge of the transmissive support 36, which may be made from a material as strong and transmissive as, e.g., quartz or sapphire, and be of a thickness on the order of about 2 mm, preferably. By contrast, the thin film 24 may preferably have thickness on the order of 1–2 mils. The exit deck portion 34" similarly comprises a substrate 102' and a Teflon coating 104' and is coupled at an interface between the transmissive support 36' and a "downstream" edge of the exit deck portion 34".

Within a treatment zone 54, an "upstream" edge of the pulsed light sterilization chamber 14 of FIG. 1, the thin film 24 slides across the transmissive support 36. As a target object 24 moves on the thin film 24 through the treatment zone 54, the thin film 24 on top of the transmissive support 36 and the transmissive support 36 allow pulsed sterilizing light from the flashlamp unit 26 below the transmissive support to penetrate all surfaces of the target object 24 without shadowing by the thin film 24 or the transmissive support 36.

The use of the transmissive support 36 and the thin film 24 improves efficiency of the sterilization process because fewer manipulations, rotations and pulses of pulsed sterilizing light are required to sterilize (or to reduce microbial activity at) the target object 24.

After sterilization of the target object 52 in the treatment zone, the thin film 24 underneath the target object 52 and the target object 52 continue moving through the treatment zone 54 onto the exit deck 34" where the target object 52 is moved to the exit drop 50 shown in FIG. 1.

Referring next to FIG. 3, a cross-sectional top to bottom planar view is shown of two flashlamp units 26 surrounding a treatment zone 54 within the pulsed light sterilization chamber 14 and system 10 shown in FIG. 1.

The two flashlamp units 26 each comprise a system of one or more reflectors 130 and one or more flashlamps 132 within each of the reflectors 130. The one or more reflectors 130 each comprise inner reflecting walls, shaped to reflect light from the one or more flashlamps 132 within each of the one or more reflectors 130 to the target object 52 in a desired pattern across the target object 52, such as uniformly.

In one embodiment, the one or more reflectors 130 are in a circular or U-shaped configuration, having a first curved (circular, elliptical parabolic, etc.) cross-section along a direction of motion of the target object 52. In an embodiment such as in FIG. 1, the one or more reflectors 130 are placed in a linear or tubular configuration along a tubular flashlamp unit from a three (3) dimensional perspective, instead of the curved (e.g., U-shaped) configuration.

In an alternate embodiment, the one or more reflectors 130 have a second curved (e.g., U-shaped) cross-section along another direction such that the one or more reflectors 130 form a 3-Dimensional curved (e.g., spherical) system about the target object 52 as it moves through the treatment zone 54.

As described earlier herein, the flashlamp unit 26, such as the PUREBRIGHT system cited above, includes a pulsing device (pulser 46) with a DC power supply that charges energy storage capacitors; a switch used to discharge the capacitors; a trigger circuit used to fire the switch at programmable time intervals, in response to sensors that detect the position of the target object 52 to be treated, or in response to a button being depressed; and a set of high voltage coaxial cables carrying the discharged pulses from a capacitor-switch assembly to the flashlamp units 26. The flashlamp units 26 include from one to eight flashlamps 132 mounted in metal reflectors 130 so as to direct the polychromatic light emitted from the flashlamps 132 toward the target object.

Figure 4:
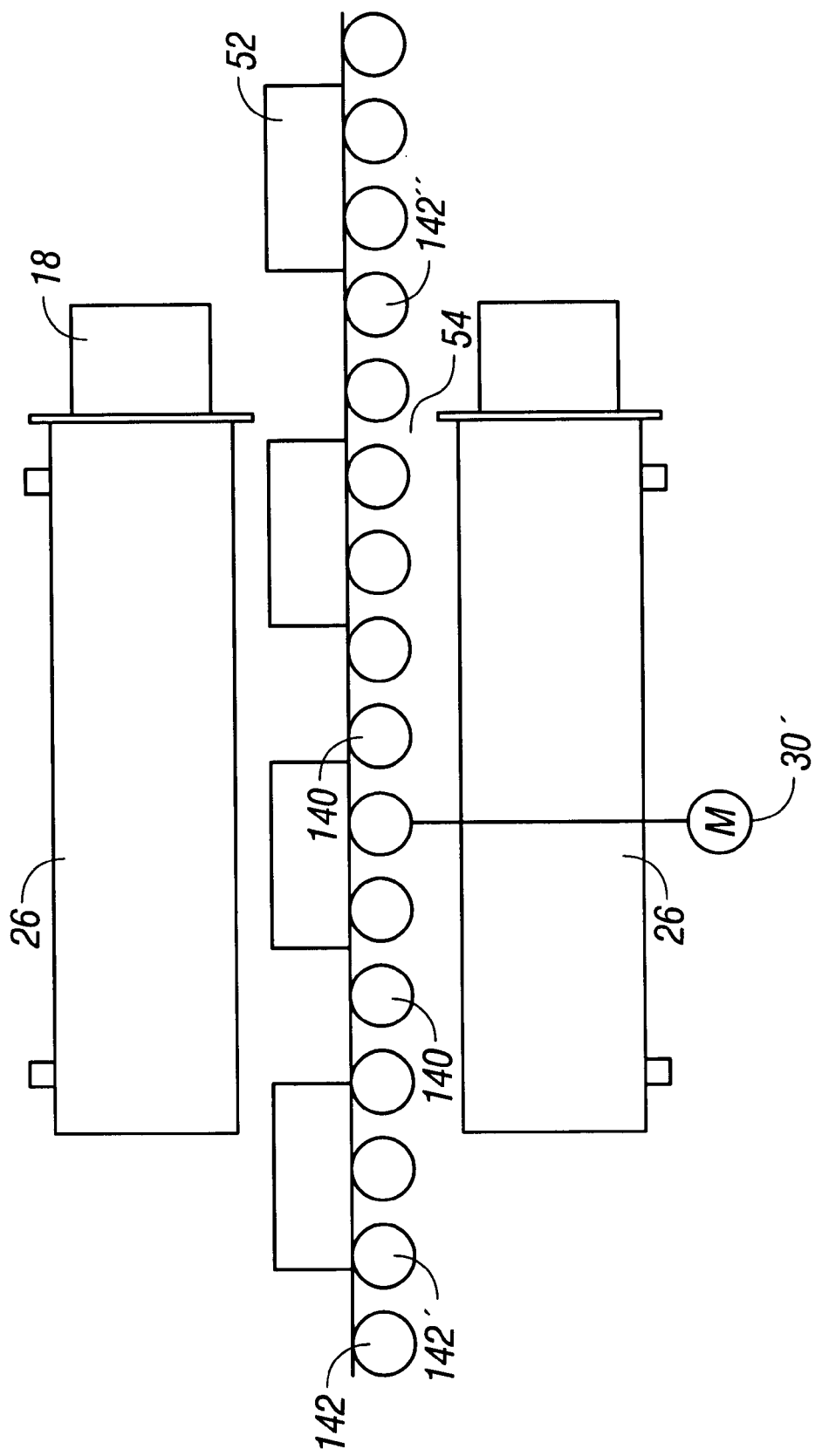
FIG. 4 is a side view of an alternate embodiment of the pulsed light sterilization chamber and system in which transmissive rollers are used as the transmission carrier in the pulsed light sterilization of a product.

Referring next to FIG. 4, a side view is shown of an alternate embodiment of a transmissive carrier that can be employed in the pulsed light sterilization chamber 14 of FIG. 1.

The pulsed light sterilization chamber 14 comprises: the treatment zone 54 illustrated in FIG. 1, and 2; the flashlamp units 26 of FIG. 1, and 3, having the electronic interface 18, pulser 46 and flash encoder 44 of FIG. 1; a plurality of transmissive rollers 140 replacing the thin film 24 of FIG. 1; and a plurality of rollers 142 replacing the slide deck of FIG. 1.

The transmissive carrier comprises the plurality of transmissive rollers 140 made from a material such as quartz or sapphire within the treatment zone 54. The plurality of transmissive rollers 140 each rotate axially around their respective major axes. The transmissive rollers 140 have a coefficient of friction which, together with a coefficient of friction of the target object 52, allows for movement of the target object 52 on the transmissive rollers 140. The plurality of transmissive rollers 140 also have a speed of rotation induced from a roller moving means 30' that determines a speed of the target object 52 through the treatment zone 54.

The roller moving means 30' (also referred as a moving means or moving mechanism) is coupled to the transmissive rollers 140 to induce rotation of the transmissive rollers 140. The roller moving means 30' may also, alternatively, be coupled to the flash encoder 44 shown in FIG. 1 to control the speed of rotation thereof.

The plurality of rollers 142 comprise a first set of rollers 142' moving the target object 52 to the treatment zone 54, and a second set of rollers 142" moving the target object 52 away from the treatment zone 54. The plurality of transmissive rollers 140 move the target object 52 through the treatment zone 54.

The target object 52 is carried to the treatment zone 54 by the rotation of the first set of rollers 142'. Upon leaving the treatment zone 54, the target object 52 is carried by the second set of rollers 142" away from the treatment zone 54.

Alternate ways of conveying the target object 52 may be conceived by a skilled artisan, such as employing a conveyor belt outside the treatment zone 54 in place of the first or second set of rollers 142', 142", or combination of rollers and conveyor belts can be used.

Figure 5:
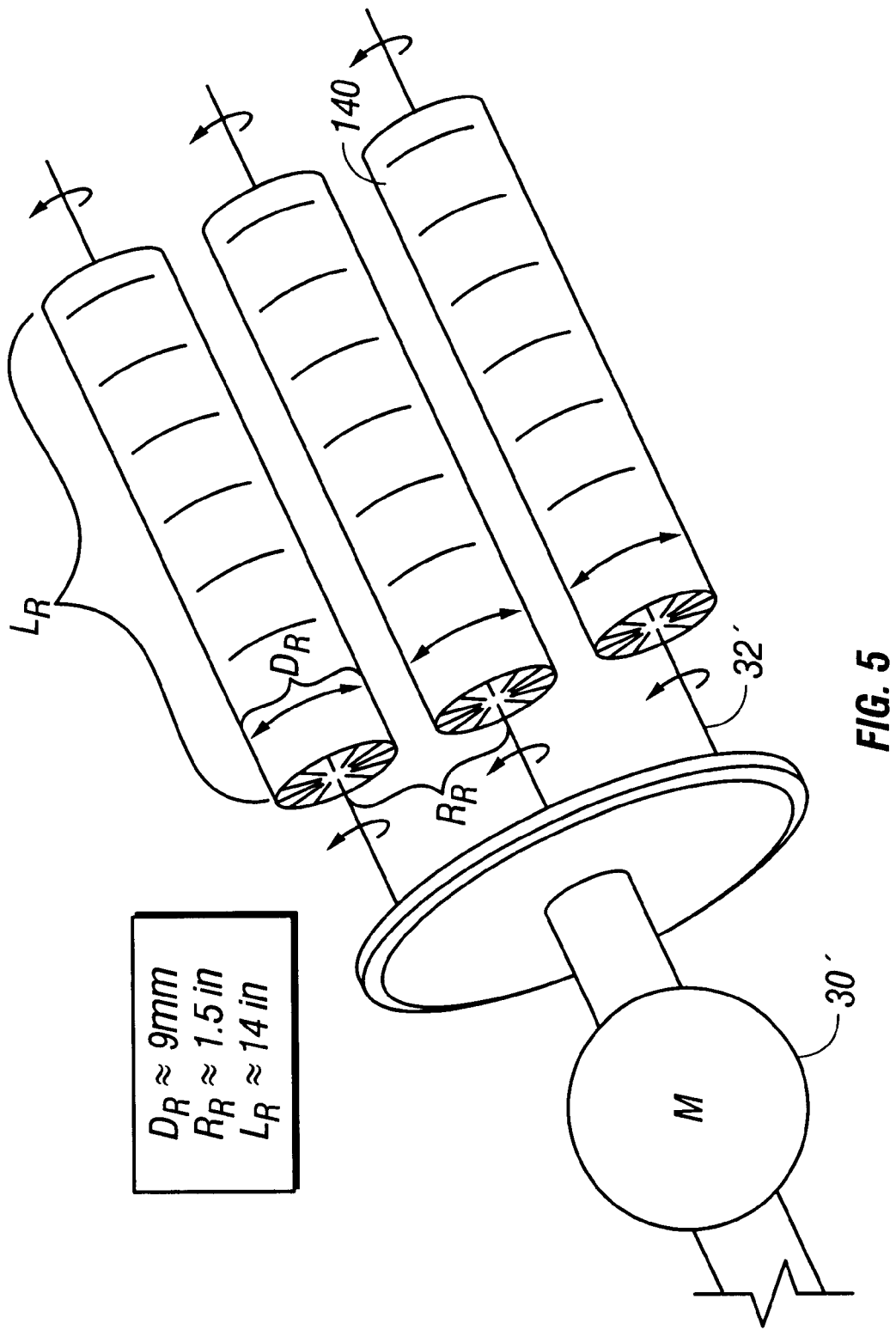
FIG. 5 is a perspective view of a plurality of transmissive rollers that may be employed in the pulsed light sterilization chamber as illustrated in FIG. 4.

Referring next to FIG. 5, a perspective view of a plurality of transmissive rollers 140 of FIG. 4 is illustrated. In one embodiment, each of the plurality of transmissive rollers 140 are nearly directly adjacent to each other, and have a major axis of about 1.5 inches from each other major axis of each other of the plurality of transmissive rollers 140. Each of the plurality of transmissive rollers 140 (and any gap between the plurality of transmissive rollers) is otherwise sized depending upon the type of target object 52 being treated. The first set of rollers 142 (FIG. 4) and the second set of rollers 142 are similarly sized and arranged.

In one variation for sterilization of relatively small containers and medical devices, each of the plurality of transmissive rollers 140 may have a diameter $D_R$ of about 9 mm and a length $L_R$ of about 14 inches to function effectively. The plurality of transmissive rollers 140 may be made of quartz or sapphire or any other material of similar strength and transmissivity having transmissivly characteristics, for example, as described above for the transmissive carrier of FIG. 1.

While the invention herein disclosed has been described by means of specific embodiments and applications thereof, numerous modifications and variations could be made thereto by those skilled in the art without departing from the scope of the invention set forth in the claims.

What is claimed is:

1. An apparatus for carrying a target object having a plurality of surfaces, within a pulsed light sterilization chamber, the pulsed light sterilization chamber including a treatment zone within which pulsed sterilizing light is emitted, the apparatus comprising:

a thin film transmissive carrier within the treatment zone detachably coupled to the target object, the thin film transmissive carrier having a transmissivity of at least about 10% to light within the 250 to 350 nm wavelength range; and moving means coupled to the thin film transmissive carrier for moving the target object on the thin film transmissive carrier through the treatment zone, the plurality of surfaces of the target object being sterilized by the pulsed sterilizing light in the treatment zone, at least a portion of the pulsed sterilizing light passing though the thin film transmissive carrier before reaching the target object.

2. The apparatus of claim 1 wherein the thin film transmissive carrier is frictionally coupled to the target object.

3. The apparatus of claim 1 wherein the thin film transmissive carrier further comprises a first rolled portion and a second rolled portion.

4. The apparatus of claim 1 wherein the moving means comprises an initial wheel containing the first rolled portion and an intake wheel containing the second rolled portion.

5. The apparatus of claim 1 wherein the thin film transmissive carrier is 80–90% transmissive in the 250 nm to 350 nm range.

6. The apparatus of claim 1 wherein the thin film transmissive-carrier is about 1 to 2 mils thick.

7. The apparatus of claim 1 wherein the thin film transmissive carrier is made of a material from a group consisting of polyethylene, polypropylene, nylon, and aclar.

8. The apparatus of claim 1 further comprising a transmissive support structure in the treatment zone underneath the thin film transmissive carrier for supporting the target object.

9. The apparatus of claim 8 wherein the transmissive support structure is about between 1 to 2 mm thick.

10. The apparatus of claim 8 wherein the transmissive support structure is made of a material from the group consisting of quartz and sapphire.

11. The apparatus of claim 10 further comprising a slide deck outside the treatment zone and adjacent to the transmissive support structure for supporting the thin film transmissive carrier until it reaches the treatment zone.

12. The apparatus of claim 11 wherein the slide deck further comprises a Teflon coating.

13. The apparatus of claim 12 wherein the slide deck further comprises a substrate below the Teflon coating.

14. The apparatus of claim 1 further comprising:

a slide deck outside of the treatment zone;

an entrance drop above the slide deck for receiving the target object into the sterilization chamber; and an exit drop below the slide deck for sending the target object out of the sterilization chamber.

15. A system for sterilizing a target object having a plurality of sides, the system comprising:

a pulsed light sterilization chamber comprising a treatment zone and means for emitting pulsed sterilizing light within the treatment zone; and a plurality of transmissive rollers within the treatment zone detachably coupled to the target object, the plurality of sides of the target object being sterilized by the pulsed sterilizing light within the treatment zone, at least a portion of the pulsed sterilizing light passing through the plurality of transmissive rollers before reaching the target object.

16. The apparatus of claim 15 wherein the pulsed light sterilization chamber emits, within the treatment zone, omnidirectional pulses of polychromatic incoherent light in a broad spectrum from 170 nm to 2600 nm with pulses from 0.001 to 100 milliseconds, the polychromatic incoherent light having an energy density of from 0.01 to 5 J/cm$^2$ at the plurality of surfaces of the target object.

17. The apparatus of claim 15 wherein the pulsed light sterilization chamber further comprises:

a plurality of open reflectors surrounding the treatment zone; and a plurality of flashlamps surrounding the treatment zone, each of the flashlamps mounted inside one of the plurality of open reflectors such that the plurality of open reflectors reflects the pulsed sterilizing light omnidirectionally toward the target object.

18. The apparatus of claim 15 wherein the plurality of transmissive rollers is frictionally coupled to the target object.

19. The apparatus of claim 15 wherein the plurality of transmissive rollers comprise material from a group of materials consisting of sapphire and quartz.

20. The apparatus of claim 1 wherein the pulsed light sterilization chamber emits, within the treatment zone, omnidirectional pulses of polychromatic incoherent light in a broad spectrum from 170 nm to 2600 nm with pulses from 0.001 to 100 milliseconds, the polychromatic incoherent light having an energy density of from 0.01 to 5 J/cm$^2$ at the plurality of surfaces of the target object.

21. The apparatus of claim 1 wherein the pulsed light sterilization chamber further comprises:

a plurality of open reflectors surrounding the treatment zone; and a plurality of flashlamps surrounding the treatment zone, each of the flashlamps mounted inside one of the plurality of open reflectors such that the plurality of open reflectors reflects the pulsed sterilizing light omnidirectionally toward the target object.

22. The apparatus of claim 15 wherein each of the plurality of rollers has an axis of rotation, the axis of rotation of each of the plurality of rollers being placed about 1.5 inches apart from another of the plurality of rollers.

23. The apparatus of claim 15 further comprising a moving means.

24. The apparatus of claim 23 wherein the moving means is coupled to the plurality of transmissive roller, the moving means moving the target object on the plurality of transmissive rollers through the treatment zone.

25. The apparatus of claim 23 wherein the moving means is bonded to the plurality of transmissive rollers.

* * * * *